(12) United States Patent
Dentinger

(10) Patent No.: US 8,050,476 B2
(45) Date of Patent: Nov. 1, 2011

(54) HEART RATE DEMODULATION OF PERIODIC MOVEMENT IN ULTRASOUND DATA FOR OBJECT IDENTIFICATION

(75) Inventor: Aaron Mark Dentinger, Latham, NY (US)

(73) Assignee: General Electric Company, Niskayuna, NY (US)

( * ) Notice: Subject to any disclaimer, the term of this patent is extended or adjusted under 35 U.S.C. 154(b) by 1303 days.

(21) Appl. No.: 11/562,631

(22) Filed: Nov. 22, 2006

(65) Prior Publication Data

US 2008/0119736 A1 May 22, 2008

(51) Int. Cl.
*G06K 9/00* (2006.01)
*A61B 8/00* (2006.01)
*A61B 6/00* (2006.01)

(52) U.S. Cl. .................... 382/131; 600/473; 600/443

(58) Field of Classification Search .............. 382/131; 600/473, 443
See application file for complete search history.

(56) References Cited

U.S. PATENT DOCUMENTS

| | | | | |
|---|---|---|---|---|
| 5,349,524 A | * | 9/1994 | Daft et al. | 600/441 |
| 5,429,137 A | * | 7/1995 | Phelps et al. | 600/455 |
| 5,560,363 A | * | 10/1996 | Torp et al. | 600/455 |
| 6,419,632 B1 | * | 7/2002 | Shiki et al. | 600/443 |
| 7,558,618 B1 | * | 7/2009 | Williams | 600/473 |
| 7,736,314 B2 | * | 6/2010 | Beach et al. | 600/437 |
| 2003/0125624 A1 | * | 7/2003 | Shiki | 600/443 |
| 2006/0079782 A1 | * | 4/2006 | Beach et al. | 600/450 |

OTHER PUBLICATIONS

"Clutter Rejection Filters in Color Flow Imaging: A Theoretical Approach" IEEE Transactions on Uutrasonics, Ferroelectrics, and Frequency Control, vol. 44, No. 2, Mar. 1997, p. 417-424.*
J.A. Jensen, "Estimation of Blood Velocities Using Ultrasound", Cambridge University Press: Cambridge, England, 1996, pp. 6-15, 154-157.
C. Kasai, K. Namekawa, A. Koyano, and R. Omoto, "Real-time two-dimensional blood flow imaging using an autocorrelation technique", IEEE Trans. on Sonics and Ultrasonics, vol. SU-32, No. 3, pp. 458-464, May 1985.
H. Torp, "Clutter rejection filters in color flow imaging: a theoretical approach", IEEE Trans. on Ultrasonics, Ferroelectrics, and Frequency Control, vol. 44, No. 2, pp. 417-424, Mar. 1997.
A.V. Oppenheim and R.W. Schafer, Discrete-Time Signal Processing, Prentice Hall: Englewood Cliffs, New Jersey, 1989, pp. 402-407.
A. Papoulis, Probability, Random Variables, and Stochastic Processes, 3rd Ed., McGraw-Hill: New York, 1991, pp. 78-79, 138-141, 264-275.
R.C. Gonzalez and R.E. Woods, "Digital Image Processing", Addison-Wesley Publishing: Reading Massachusetts, 1992, pp. 40-43.
M. Skolnik, "Introduction to Radar Systems", 2nd. Ed., McGraw-Hill: New York, 1980, pp. 392-395.

* cited by examiner

*Primary Examiner* — Wenpeng Chen
(74) *Attorney, Agent, or Firm* — Jenifer E. Haeckl

(57) ABSTRACT

The systems and methods enhance, or increase the strength of, signals collected from a target object, to facilitate identification of the object, by removing or suppressing signal variations or aberrations associated with the object or its surroundings.

2 Claims, 12 Drawing Sheets

Brachial Artery  No Artery Present

HEART RATE DEMODULATION OF PERIODIC MOVEMENT IN ULTRASOUND DATA FOR OBJECT IDENTIFICATION

BACKGROUND

The invention relates generally to systems and method for enhancing movement related data to detect objects such as blood vessels.

Doppler processing techniques are commonly used in medical ultrasound machines for obtaining velocity information from moving objects. The velocity measured using ultrasound Doppler techniques is the radial component of the velocity directed toward or away from the ultrasound transducer. Two common modes are continuous wave (CW) and pulsed wave (PW) Doppler acquisitions. One advantage of the pulsed wave acquisition is the ability to produce velocities estimates at multiple depths along the beam direction locations allowing a two-dimensional image of the velocities to be formed. The pulsed wave data acquisition consists of transmitting a series of ultrasound pulses at a regular rate, referred to as the pulse repetition rate (PRF), in a given direction. For each transmitted pulse, the RF waveform of the returning echoes is collected as a function of time. Real-time processing techniques, such as the autocorrelation method, can be applied to the data from a PW Doppler acquisition to produce an estimate of the velocities. The depth of the object causing the backscattered echoes is found by converting the time in the RF waveforms to a distance along the direction of the ultrasound beam using the speed of sound in the medium. Previous attempts to use ultrasound data to detect blood vessels were insufficient.

BRIEF DESCRIPTION

One or more embodiments of the systems and methods are generally designed to optimize blood flow data collected by a medical ultrasound scanner wherein the technical effect is to identify blood vessels and to enhance images of blood vessels. Such systems and methods provide improved visualization of the vessels allowing vessels to be more easily identified from the surrounding tissue. Some of the embodiments of the systems and methods enhance the signals from pulsating blood flow to facilitate identification of the vessels. The systems and methods use data of the subject's heart rate to effectively remove the periodic variation in the blood velocities and to suppress components of the blood flow signal that differ from the heart rate. The resulting processed data can then be used to automatically detect one or more vessels and/or to enhance the display an image of the vessel, for example, in a display provided in an ultrasound system.

The ability to measure blood flow both non-invasively and in real-time is one of the advantages of medical ultrasound. By increasing the strength of signal strength from a pulsating artery, the systems and methods of the invention are able improve the robustness of detection systems and allow automated detection of the artery without user intervention. The heart rate demodulation embodiments of the methods are generally adapted to use information about the heart rate to enhance the signal in ultrasound data from objects with periodic motion at that same rate. Although one or more embodiments of the methods are provided for automatically detecting objects and for enhancing such objects for display, the invention is not limited to these embodiments. These systems and methods will benefit virtually any application in which identification of vessels or other similar objects is desired or required.

An embodiment of the method for enhancing a signal of a target object generally comprises the steps of: providing a rate of periodic movement of the target object; and demodulating the rate of the target object, wherein the rate of movement may be expressed as a complex-valued autocorrelation sequence and wherein the step of demodulating comprises the step of down-mixing the autocorrelation sequence. The step of down-mixing preferably comprises the steps of: providing a complex phasor having a unity amplitude that is rotating at a constant frequency substantially equal to the heart rate; and multiplying the autocorrelation sequence by the complex phasor. The step of demodulating may also comprise the step of applying a low pass filter to the autocorrelation sequence, wherein the low pass filter may comprise a digital, frequency selective filter. The rate of movement may be directly derived from the raw complex autocorrelation function and may further be provided by an external source.

One or more embodiments of the method may further comprise the steps of: calculating the statistic properties of one or more pixels without periodic movement corresponding noise pixels for this application; determining an adaptive threshold for a magnitude of one or more object pixels based on one or more properties of the noise pixels; identifying the object pixels based on the threshold with positive or negative average velocities; assigning labels to one or more of the object pixels that are substantially adjacent; and locating the adjacent object pixels that define one or more objects based on one or more size and/or power criteria.

An embodiment of the system for automatically detecting an object associated with a rate of movement, generally comprises: a processor for filtering a complex autocorrelation signal corresponding to the rate of movement; demodulating the filtered complex autocorrelation signal; calculating one or more statistics of one or more noise pixels corresponding to objects without periodic movement; determining an adaptive threshold for a magnitude of one or more object pixels based on one or more properties of the noise; identifying the object pixels that correspond to one or more positive and negative velocities based on the threshold; assigning labels to one or more of the object pixels that are substantially adjacent; locating the adjacent object pixels that define one or more of the objects based on one or more size and power criteria; and creating an image that comprises one or more of the detected objects; and a display device for displaying the image of the detected object.

An embodiment of the method for displaying an object, generally comprises the steps of: providing a rate of movement of the target object; demodulating the rate of movement of the target object to produce a demodulated signal; computing a power of the demodulated signal; creating an image sequence, based on the power of the demodulated signal, that comprises one or more enhanced periodic motion pixels; and combining the image sequence of the enhanced periodic motion pixels with a second image sequence to form an image display, wherein the step of computing may comprises taking a magnitude of one or more autocorrelation pixels. The second image may comprise a B-Mode image from an ultrasound scanner, wherein the display may comprise a duplex display that may be displayed on a monitor such as an ultrasound monitor. The method may be embodied in a system such as a system that comprises: a processor that: demodulates the provided rate of movement of the target object to produce a demodulated signal; computes the power of the demodulated signal; creates the image sequence, based on the power of the demodulated signal, that comprises the enhanced periodic motion pixels; and combines the image sequence of the enhanced periodic motion pixels with a second image sequence to form an image display; and a display device that displays the image.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The heart rate demodulation embodiment of the methods and systems may be applied directly to the raw samples from a standard Doppler color flow acquisition, generally referred to as the complex autocorrelation function at a single frame lag. Components of the blood flow signal at frequencies that differ from the heart rate are suppressed by applying digital filtering techniques directly to the complex autocorrelation samples. The heart rate can be obtained from another modality (such as ECG or pulse oximetry), directly from the ultrasound data itself, or from nominal values for the physiological range. The implementation used in the development of the invention included complex demodulation of the autocorrelation samples followed by a lowpass filter. The demodulation step converts the velocities pulsating at the heart rate to constant signal levels and the lowpass filter attenuates components of the velocity varying at frequencies other than the heart rate, including the harmonics of the heart rate. The result of the processing is a new set of complex autocorrelation samples with the power in the signal enhanced and the heart rate variation removed. The amplitude of the complex autocorrelation samples can then be used to determine the location of vessel when displayed by the system or used in an automatic vessel detection application. The phase of the average complex autocorrelation can also be used as an indication of the average blood velocities over the cardiac cycle and discriminate pulsating flow in opposite directions.

The velocity measured using ultrasound Doppler techniques is the radial component of the velocity directed toward or away from the ultrasound transducer. As noted, one of the common modes is pulsed wave Doppler acquisition. One advantage of the pulsed wave acquisition is the ability to produce velocities estimates at multiple depths along the beam direction locations allowing an image of the velocities to be formed. The pulsed wave data acquisition transmits a series of ultrasound pulses at a regular rate in a given direction and collects the RF waveforms of the returning echoes as a function of time. The depth of the object causing the backscattered echoes is found by converting the time in the RF waveforms to a distance along the direction of the ultrasound beam using the speed of sound in the medium.

Any relative motion of an object away from or toward the ultrasound transducer introduces a Doppler shift in the returning ultrasound waveform. Autocorrelation is one method used to estimate the Doppler shift for the range samples in a pulsed wave acquisition. The Doppler shift is estimated directly from analysis of the raw RF waveforms or equivalently from analysis of its complex envelope, such as produced from the real and imaginary parts of a quadrature detector.

Figure 1:
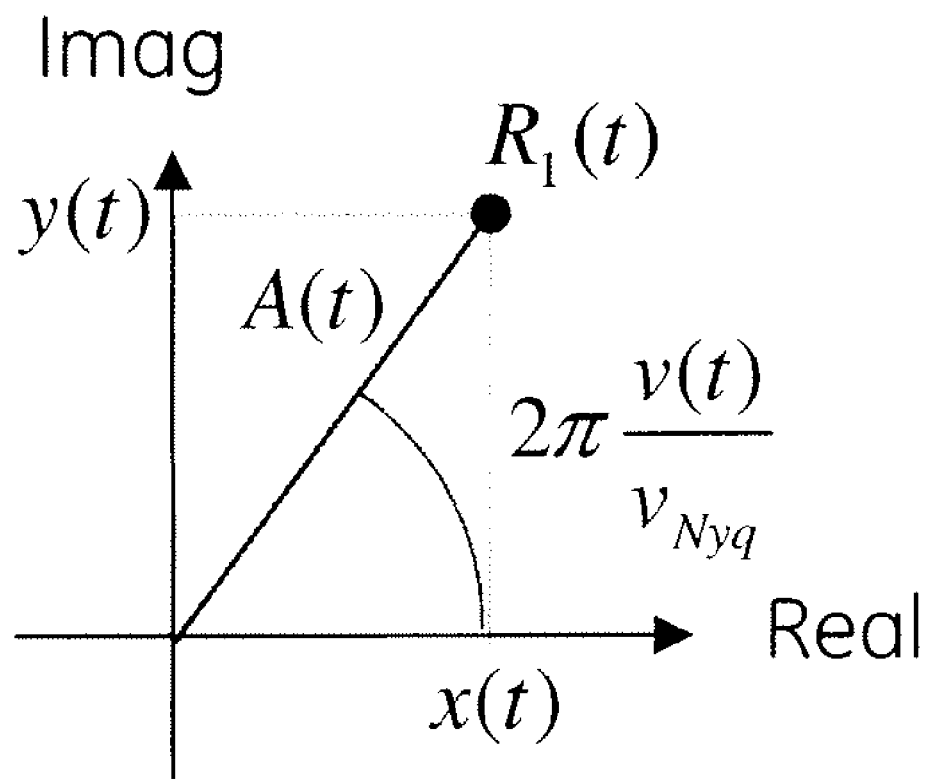
FIG. 1 is a graph of the relationship between an embodiment of the complex autocorrelation function to object velocity.

When applied to the complex envelope, the autocorrelation function is complex-valued and the velocity is calculated from the phase of the autocorrelation function for discrete range samples with a temporal delay of one firing. This relation between the complex autocorrelation function ($R_1$) and the velocity (v) is summarized in FIG. 1 and by the following equation $$R_1(t) = A(t) e^{j2\pi \frac{v(t)}{v_{Nyq}}}$$

where A is the amplitude of the complex autocorrelation function and $V_{Nyq}$ is the Nyquist velocity. The Nyquist velocity represents the maximum velocity that can be observed without aliasing and is given by $$v_{Nyq} = \frac{cPRF}{4f_{RX}}$$

where c is the speed of sound in the medium, $f_{RX}$ is the center frequency of the received RF signal, and PRF is the pulse repetition frequency corresponding to rate at which the ultrasound beams are fired in the same direction.

As an alternative to the magnitude and phase representation, the complex autocorrelation function may also be represented as the sum of a real and imaginary components $$R_1(t) = x(t) + jy(t)$$

where x and y are the real and imaginary components, respectively.

In its basic form, the pulsed wave acquisition provides velocity information for discrete range samples along a one-dimensional line corresponding to the ultrasound beam. A two-dimensional velocity data set is formed by sweeping the direction of the ultrasound beam within a scan plane and performing a series of one-dimensional pulsed wave data acquisition for each beam direction in the sweep. Each beam direction corresponds to a single line in a 2-D image. The same steps may also be applied to three spatial dimensions to produce velocity data within a volume.

In addition to being sampled spatially, autocorrelation, and hence the velocity, are preferably sampled at discrete times corresponding to the times when the pulsed wave acquisition is repeated in the same direction. These discrete times are assumed, for the purpose of this step, to occur at a regular rate, which for the 2-D pulsed wave acquisition is equal to the frame rate of the image sequence. The discrete-time sequence of the autocorrelation function is related to the continuous time waveform by $$R_1[n]=R_1(nT_s+t_0) \text{ for } n=0,1,2,$$

where n is the discrete time index, $T_s$ is the sampling period, and $t_0$ is time for the first sample.

Two examples of clinical objects, that may be identified and/or enhanced for display, that produce periodic motion at the heart rate include, but are not limited to, the velocity of the red blood cells in an artery or the movement of the walls and valves in a fetal heart. When one or more of the methods are applied to blood flow, an additional preprocessing step is preferably used to suppress the signal from stationary objects allowing the smaller signal from the red blood cells to be observed. This preprocessing step is referred to as clutter or wall filtering.

Figure 2:
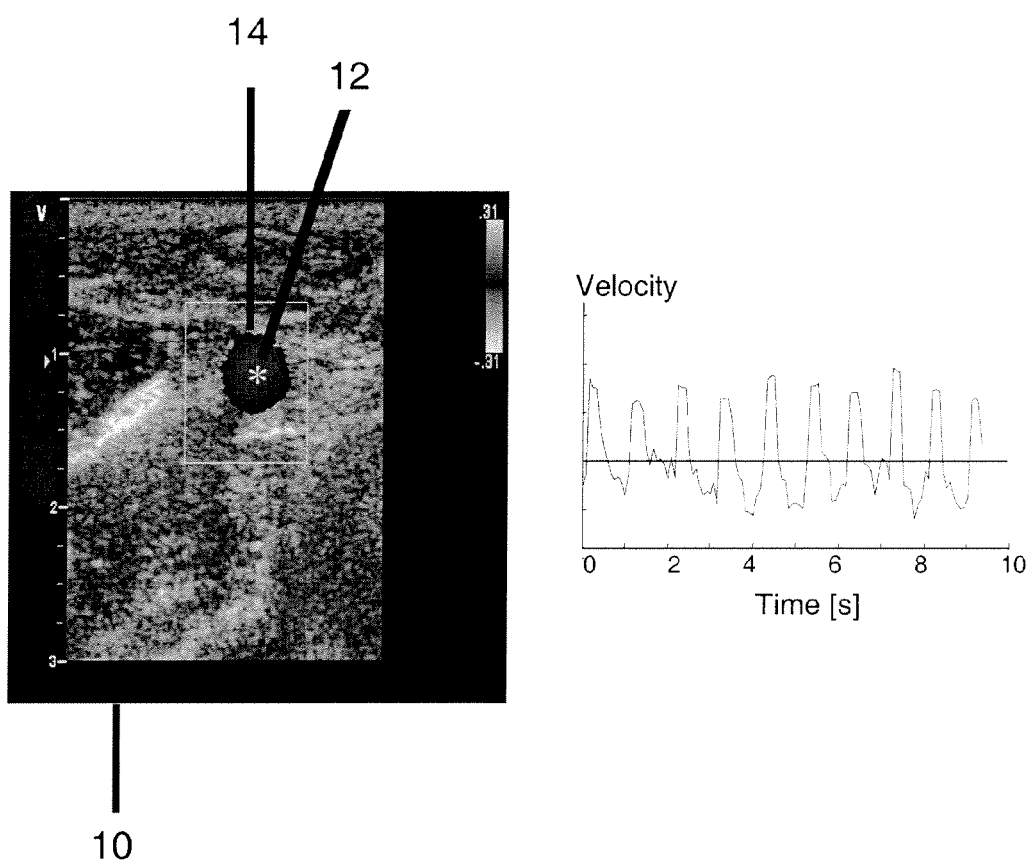
FIG. 2 is an image and graph of an arterial based embodiment of an image of an identified vessel and the periodic blood velocity waveform.

One example of the periodic velocities produced in one of the arterial embodiments is shown in FIG. 2. The data was acquired on a GE Vivid 7 ultrasound scanner in 2-D color flow mode using a GE M12L ultrasound probe, and the standard Doppler processing available on the system was used to generate the velocity waveforms. The ultrasound image 10 on the left in FIG. 2 is a single frame of a human common carotid artery taken in the color flow acquisition mode on the Vivid 7. The velocity information is encoded with the color and is overlaid on the B/W image. A temporal waveform of the blood velocity is shown in the graph on the right for a small region within the center of the vessel 14 marked by the asterisk 12 in the image. The heart rate for this embodiment was approximately 60 beats per minute.

The heart demodulation step is designed to optimally work on the individual discrete range samples of the complex autocorrelation sequence from an ultrasound pulsed wave Doppler acquisition. The demodulation step is applicable to the autocorrelation sequence produced either with or without a clutter filtering, so it is therefore applicable, but not limited, to blood flow and tissue velocity images.

Demodulation is used in many fields to remove the variation in the signal occurring at a known rate, such as in communication applications to recover the original signal that has been modulated with a carrier frequency prior to transmission. However, unlike these example uses, one or more of the methods of the invention further use another property of demodulation to suppress variations that do not occur at the given rate.

The heart rate (HR), defined as the number of heart beats in specified time interval typically measured in beats per minutes (BPM), is a commonly measured vital sign in the medical field. Automatic heart rate measurements can be derived from a number of modalities, such as from ECG or pulse oximetry waveforms. Heart rate measurements can be obtained using a variety of medical devices and instruments such as, but not limited to, blood pressure machines, ultrasound scanners, or patient monitor. Any one or more of these sources of heart rate data may be used in the systems and methods of the invention.

However, in instances in which the exact heart rate is not known or otherwise available, a range of values for the expected heart may be used to define the parameters in the HR demodulation step. For example, if the expected frequency range is defined by $f^{(L)}$ and $f^{(U)}$, then the demodulation frequency can be selected as the center of this frequency band and computed using the equation below $$f_{HR} = \frac{(f^{(U)} - f^{(L)})}{2}.$$

Figure 3:
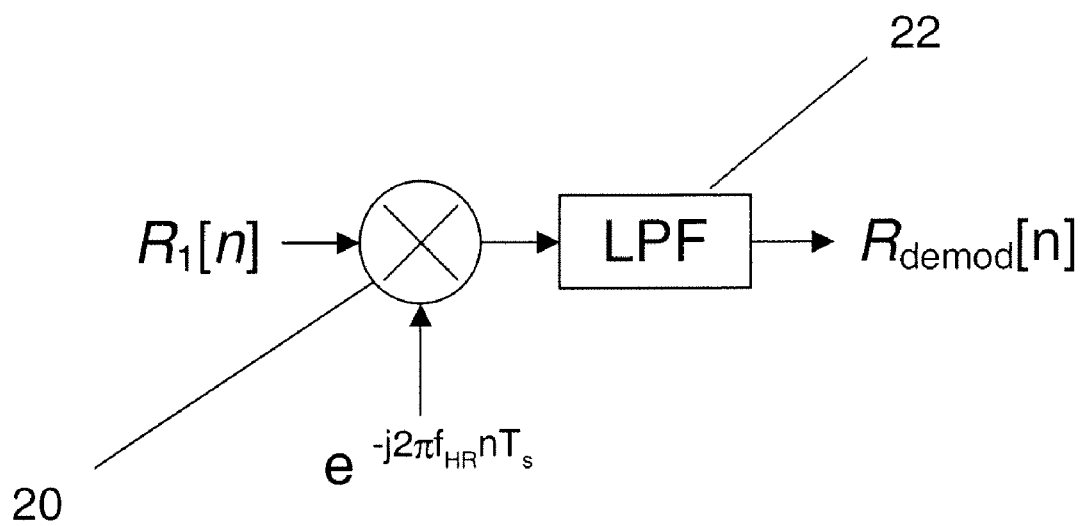
FIG. 3 is a schematic diagram of an embodiment of the heart rate demodulation steps.

The heart rate demodulation of the complex autocorrelation function consists of two main steps: down-mixing and lowpass filtering. For the discrete-time autocorrelation sequence, these two steps are implemented digitally and are depicted in FIG. 3. The down-mixing step shifts the frequency components of the complex autocorrelation sequence, that are varying at the heart rate, to zero frequency. The down-mixing is accomplished by multiplying the autocorrelation sequence by a complex phasor of unity amplitude that is rotating at a constant frequency equal to the heart rate. In FIG. 3, the circle containing the multiplication symbol illustrates the down-mixing step 20. The down-mixing can be illustrated as $$R_{mixed}[n_t]=R[n_t]e^{-j2\pi f_{HR} n_t T_s}$$

where $n_t$ is the discrete time index, $f_{HR}$ is the frequency of the heart rate in Hz, and $T_s$ is the sampling period in seconds. A heart rate in BPM can be converted to a temporal frequency in cycles per second (Hz) by dividing it by 60.

The down-mixing may also be implemented on the real and imaginary components of the autocorrelation by using Euler's formula to represent the complex exponential as $$e^{j\theta}=\cos\theta+j\sin\theta.$$

The down-mixing applied to the real component is $$x_{mixed}[n_t]=x[n_t]\cos(2\pi f_{HR} n_t T_s)-y[n_t]\sin(2\pi f_{HR} n_t T_s)$$

and the imaginary component is $$y_{mixed}[n_t]=x[n_t]\sin(2\pi f_{HR} n_t T_s)+y[n_t]\cos(2\pi f_{HR} n_t T_s).$$

The down-mixing step is followed by a lowpass-filtering step 22 whose purpose is to suppress the high frequency components in the sequence while allowing the lower frequencies to pass unattenuated. The lowpass filtering step 22 in this embodiment is accomplished by applying a digital, frequency-selective filter to the complex autocorrelation sequence. The desired properties for the lowpass filter will be specified in the frequency domain and these properties are independent of the filter type and implementation.

Figure 4:
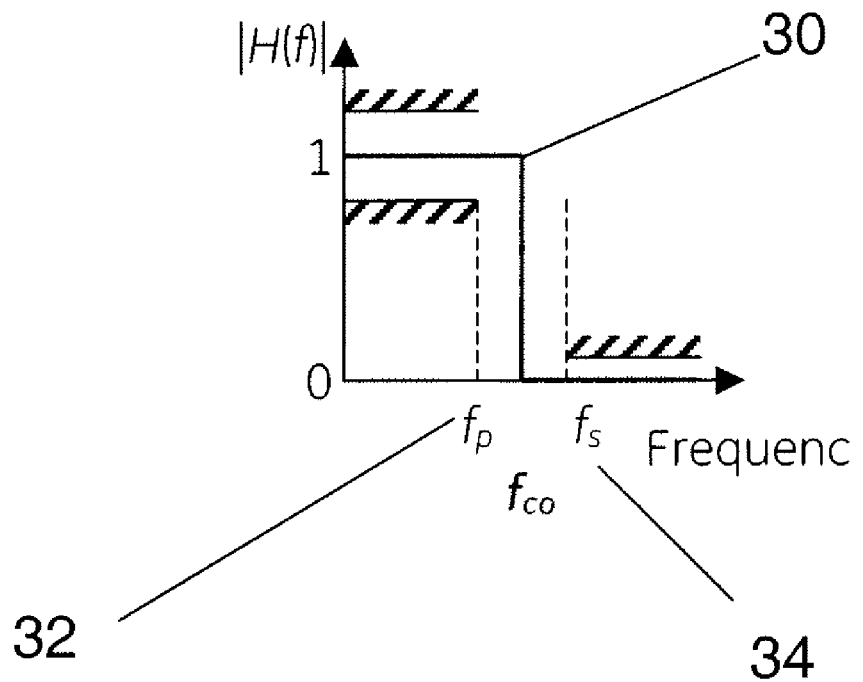
FIG. 4 is a graph of the frequency domain specification of an example of a low pass filter used in one or more embodiments.

The magnitude of the frequency response for a preferred embodiment of the lowpass filter is shown as curve 30 in FIG. 4. The curve is shown for positive frequencies only since a real-valued filter will have even symmetry of its magnitude in the frequency-domain. The ideal frequency response has unity magnitude for all frequency below a cutoff frequency, $f_{co}$ and zero magnitude for frequencies above the cutoff frequency. In FIG. 3, the lowpass filter step is generally referred to as LPF step 22.

For the HR demodulation, the desired cutoff frequency is determined from the heart rate frequency used for the down-mixing. A fraction of this frequency may be used to specify the cutoff frequency resulting in the attenuation of frequency components in the original autocorrelation sequence that are not within a given frequency band around the heart rate frequency.

The desired frequency-domain specifications may be approximated using a causal discrete-time system, such as an infinite impulse response (IIR) or and finite impulse response (FIR) filter. Known design tools are available for creating both IIR or FIR filters from frequency domain specifications. Either of these types of filters may be utilized in the HR demodulation step. Some of the methods required additional parameters beyond the cutoff frequency to be specified, such as the width of the transition phase and the deviation away from the desired magnitude in the passband and stopband. These additional frequency domain specifications are also shown in FIG. 4. Once an IIR or FIR filter is identified and optimized for a given application, the filter may be implemented on a digital computer or processor using a representation of the causal discrete time system.

The HR demodulation step preferably selects the components of the waveform corresponding to positive frequencies. The same step may be applied to the components from negative frequencies and the results may be combined to use information from positive and negative frequencies. One example of an embodiment of the heart rate demodulation steps is based at least in part on the data from the arterial example described above.

Figure 5:
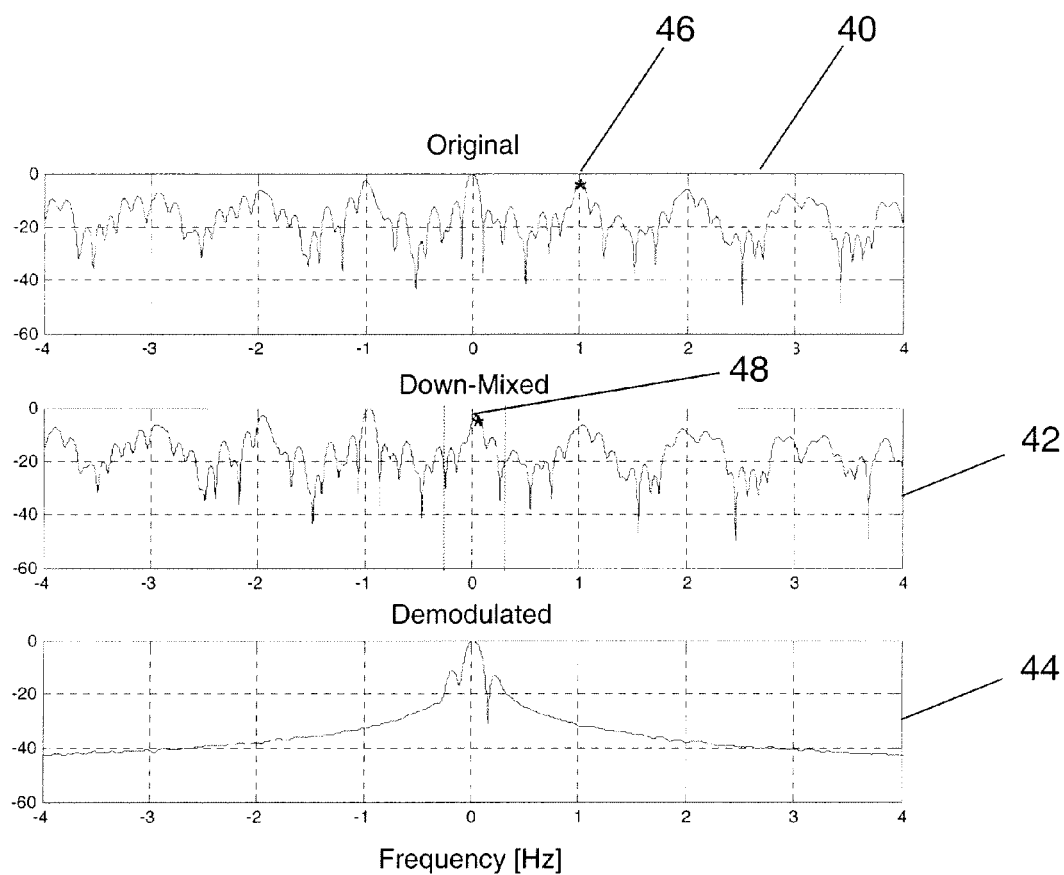
FIG. 5 is a series of graphs showing examples of spectra of original, down-mixed, and demodulated autocorrelation sequences from an embodiment of the methods and systems.

FIG. 5 shows the spectra of the signals at different points in the HR demodulation processing chain. Graph 40 at the top of FIG. 5 shows the spectrum of the original complex autocorrelation sequence created by taking the discrete Fourier transform. The horizontal axis corresponds to the frequency of the DFT coefficients. For the original sequence, peaks in the spectrum are observed at DC, the heart rate, which for this example is approximately 60 BPM or 1 Hz, as well as at harmonics of the heart rate.

Graph 42 of FIG. 5 shows the spectrum after down-mixing by the heart rate frequency. Down-mixing shifts the spectrum in the frequency domain as indicated by the movement at peak at 1 Hz in the original waveform asterisk 46 to near zero frequency in the down-mixed spectrum at asterisk 48. This peak is now centered at DC (zero frequency) and application of the lowpass filter will cause the other peaks to be attenuated leaving only one dominant peak. This is shown by the demodulation spectrum in the lower graph 44.

Figure 12:
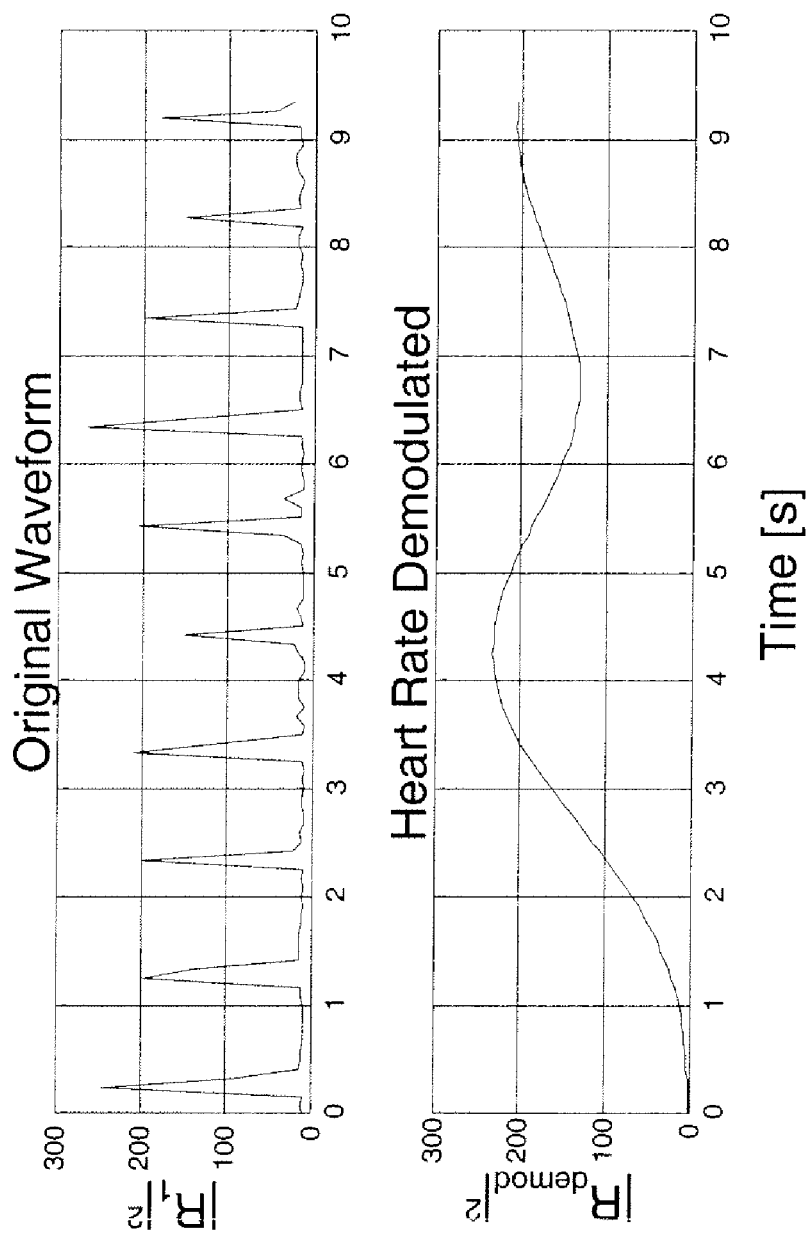
FIG. 12 shows two graphs of an embodiment of the magnitude of autocorrelation function as a function of time for the original data (top) and the heart rate demodulated data (bottom).

The effect of the HR demodulation processing in the time domain is shown by the magnitude of the complex autocorrelation sequence in FIG. 12 before and after the HR demodulation processing for a pixel near the center of the vessel. The periodic variation at the heart rate for the original waveform has been removed by the processing. The residual variation in the demodulated waveform is due to the step response of the low-pass filter in the demodulation processing, and the oscillations around the steady state value will continue to decay as more frames are acquired.

Since the heart rate demodulation suppresses signals from objects not moving periodically at the heart rate, two example applications in which the HR demodulation may be applied include, but are not limited to, automatically detecting objects whose motion is the result of a beating heart and enhancing such objects for display. For example, two anatomical targets for one or more of the embodiments may include, but are not limited to, an artery containing pulsating flow and a beating fetal heart. For the vascular targets, veins may also be targets in certain circumstances such as, but not limited to, when the vein is temporarily occluded proximal to the measurement location to increase the venous pressure and pulsatility of the venous blood flow.

Figure 6:
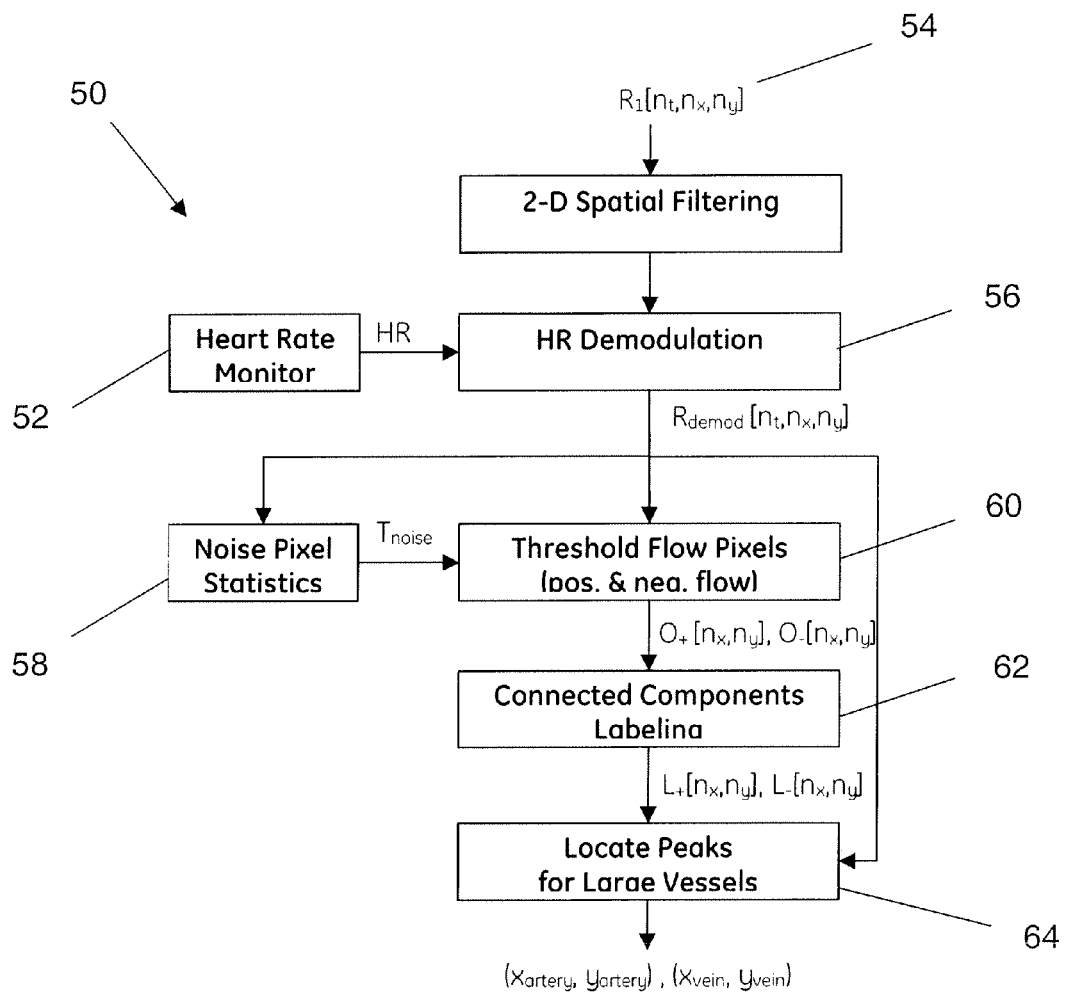
FIG. 6 is a block diagram of a plurality of steps in an embodiment of the methods and systems for automatic object detection.

An example embodiment of the method and system, for automatically detecting an object, is illustrated using a block diagram in FIG. 6. FIG. 6 generally shows the steps of one more of more embodiments of the method and system 50 for automatic objection detection using HR demodulation. One of the embodiments preferably uses two types of input data: the heart rate from monitor 52 and the complex autocorrelation function from a 2-D pulsed wave acquisition 54, that may be expressed as $R_1[n_t,n_x,n_y]$. The two other variables in the expression, $n_x$ and $n_y$, represent the indices for the spatial location of the pixel within the scan plan.

The method for automatically detecting an object may comprises the steps of: spatial filtering the complex autocorrelation function; demodulating using the HR, calculating the statistics of the non-moving (noise) pixels, determining an adaptive threshold for the magnitude of the object pixels based on properties of the noise, identifying the object pixels corresponding to positive and negative velocities using the threshold, assigning labels to connected groups (components) of object pixels, and locating connected components that contain objects using the size and power criteria.

The data from the autocorrelation function may be preprocessed using standard spatial filtering techniques to increase the signal to noise ratio before performing the detection processing. This includes standard 2-D spatial filtering applied directly to the complex autocorrelation function with the spatial extent of the filter being determined by the expected size of the object.

The first block 56 is the HR demodulation and is described previously. After the HR demodulation has been applied, a sequence of frames corresponding to the demodulated autocorrelation function, $R_{demod}[n_y,n_x,n_y]$ is available. The remaining processing is applied to a single frame of the demodulated autocorrelation taken a sufficient number of frames from the starting frame to allow the lowpass filter to reach a steady state. The number of frames can be set to a time period equivalent to several cardiac cycles.

In the 2-D ultrasound data, the pixels with periodic motion (such as pixels within an artery) are surrounded by a large number of pixels corresponding to tissue that is stationary or has non-periodic motion. These pixels will be considered noise pixels for the object identification problem. Both the real and imaginary components of the complex autocorrelation for the noise pixels will be significantly reduced by the HR demodulation. Therefore, the property of the noise pixels exploited for the identification is the magnitude of the demodulated autocorrelation function. The statistics of the magnitudes for the noise pixels may be estimated.

One or more of the embodiments of the methods assumes that the real and imaginary components of the noise pixels are independent and identically distributed from zero-mean Guassian distributions with the same variance, and based on these assumptions, the magnitude of the noise pixels then have a Rayleigh distribution whose shape may be captured by a single parameter.

The cumulative distribution function (CDF), the probability of the random variable being less than a given value, for a Rayleigh distribution is given by $$\begin{aligned} F_{Rayleigh}(z) &= P\{z \le z\} \\ &= 1 - P\{z > z\} \\ &= 1 - e^{-\frac{z^2}{2s^2}} \end{aligned}$$

where z is the magnitude of the pixel and s is the parameter for the Rayleigh distribution.

The noise pixel statistics step 58 in FIG. 6 provides an estimate of the parameter for the Rayleigh distribution by analyzing the histogram of pixel magnitudes in a single frame after application of the HR demodulation. Since the noise pixels have lower amplitudes than the objects pixels, a percentage of the lowest amplitude histogram bins will be dominated by noise. The noise parameters are determined by truncating the histogram to comprise a certain percentage of the lowest amplitude bins, and then search for the Rayleigh parameter that best fits the truncated histogram. The search is repeated for a one or more truncated histograms comprising different number of bins and the final estimated of the noise statistic uses the truncated deviation with the smallest normalized deviation from an ideal Rayleigh distribution.

One or more embodiments of the methods comprise the following steps to determine the noise parameter. The order of the steps of the methods are not necessarily limited to this example. First, the histogram of amplitudes is determined for all the pixels in the HR demodulated frame. The size of the bins should be selected to ensure a non-zero number of amplitudes fall within the lower amplitude bins. Given the lower and upper edges of the histogram bins, $x_i^{(L)}$ and $x_i^{(U)}$ respectively, the number of pixels, $k_i$, following within each histogram bin is found for $i=1, \ldots, N_{bins}$.

Second, determine the index for the upper bin used to truncate the histogram for a set of percentiles, $\{u_1, u_2, \ldots, u_{N_{perc}}\}$. The index of the upper bin for the $u_n^{th}$ percentile is the maximum integer $M_n$, such that $$\sum_{i=1}^{M_n} k_i \leq u_n N_{pixels}$$

where $N_{pixels}$ is the total number of pixels within the image, and $u_n$ is the percentiles specified as a fraction between 0 and 1.

The next step of the example of the method searches for the parameter, $\hat{s}_n$, that minimizes the deviation with the observed frequencies of occurrence for the truncated histogram and the expected probability of occurrence for an ideal Rayleigh distribution. The Pearson's test statistic [Papoulis] is used to define the deviation and is given by $$q(s, M_n) = \sum_{i=1}^{M_n} \frac{(k_i - N_M p_i(s))^2}{N_M p_i(s)}$$

where $$N_M = \sum_{i=1}^{M_n} k_i$$

is the number of pixels in the truncated histogram and $p_i(s)$ is the expected probability for a Rayleigh distributed random variable to be in the $i^{th}$ histogram bin given the parameter s.

This probability is given by $$p_i(s) = P\{x_i^{(L)} < x \leq x_i^{(U)}\}$$
$$= F_{Rayleigh}(x_i^{(U)}) - F_{Rayleigh}(x_i^{(L)})$$
$$= e^{-\frac{x_i^{(L)2}}{2s^2}} - e^{-\frac{x_i^{(U)2}}{2s^2}}$$

where $F_{Rayleigh}$ is the CDF of the Rayleigh distribution defined above. The estimate of the Rayleigh parameter is found by performing a one-dimensional search for the value of s that minimizes the deviation for the given truncated histogram, and is given by $$\hat{s}_n = \arg\min_s \{q(s, M_n)\}.$$

This repeated for each of the $N_{perc}$ truncated histogram.

The percentile that best fits a Rayleigh distribution is then determined. For this purpose, the lowest deviation is desired. The absolute deviation is not a fair comparison since the number of bins in the calculation of the deviation differs for each truncated histogram. To allow the deviations from the different truncated histograms to be compared, a $\chi^2$ (chi-square) distribution is assumed for the distribution of the deviations. The $\chi^2$ distribution is widely used in statistics for the application in testing the goodness of fit of a histogram to a given distribution.

The deviation is normalized to a value between 0 and 1 using the cumulative distribution function for the $\chi^2$ distribution. This normalization converts the deviation to a probability that a random sampling of $\chi^2$ distributed is less than the observed deviation. The better values of the deviations still having a lower valued for the CDF.

For each deviation, $q_n = q(\hat{s}_n, M_n)$, the CDF of the $\chi^2$ distribution is calculated for M−1 degrees of freedom and is given by $$\lambda_n = F_{\chi^2}(q_n \mid M_n - 1) = \int_0^{q_n} \frac{t^{(M_n - 3)/2} e^{-t/2}}{2^{(M_n - 1)/2} \Gamma((M_n - 1)/2)} dt.$$

[Reference Papoulis]

The percentile and truncated histogram with the minimum CDF is selected as the best fit $$n^* = \arg\min_n \{\lambda_n\}$$

and the corresponding parameter for the Rayleigh distribution $$\hat{s}' = \hat{s}_{n^*}.$$

is used for the noise statistic.

For a given application the pixels associated with a target object are identified. The object pixels are identified by thresholding the magnitude in step 60 of the complex autocorrelation function for the pixel in a single frame using an adaptive value based on the noise statistics. The adaptive threshold is found using the parameter for the Rayleigh distribution. The value is determined by specifying the probability that a noise pixel from a Rayleigh distribution will be incorrectly classified as an object pixel. This probability of falsely detecting a noise pixel may be set very low since the magnitude of the object pixels should be well above the stationary pixels after HR demodulation.

An expression for the threshold may be determined using the cumulative distribution function (CDF) for a Rayleigh distributed random variable. The adaptive threshold may calculated from the specified probability of falsely labeling a noise pixel and the expression for the Rayleigh CDF, yielding $$T_{noise} = s\sqrt{2\ln(P_{FA})}$$

where s is the parameter of the Rayleigh distribution and $P_{FA}$ is the desired probability of incorrectly labeling a noise pixels. The adaptive threshold is equivalent or similar to multiplying the parameter in the Rayleigh distribution by a constant scale factor.

Any pixel with a magnitude above this threshold is considered an object pixel and assigned a value of 1. This results in a binary image identifying the object pixels and is found by $$O[n_x, n_y] = \begin{cases} 1 & \text{if} |R_{demod}[n_x, n_y]| \geq T_{noise} \\ 0 & \text{otherwise} \end{cases}$$

The flow pixels may be further separated into object pixel with average motion toward or away from the transducer. This additional classification is useful to differentiate directional motion, such as from arteries and veins. The binary image for object pixels with average velocity toward the transducer is given by $$O_+[n_x, n_y] = \begin{cases} 1 & \text{if} |R_{demod}[n_x, n_y]| \geq T_{noise} \text{ and } \angle\left(\sum R_1[n_x, n_y]\right) > 0 \\ 0 & \text{otherwise} \end{cases}$$

where the summation is taken over the discrete-time samples corresponding to a single cardiac cycle and $\angle$ is the angle of the complex number.

The binary image for object pixels with average velocity away from the transducer is given by $$O_-[n_x, n_y] = \begin{cases} 1 & \text{if} |R_{demod}[n_x, n_y]| \geq T_{noise} \text{ and } \angle\left(\sum R_1[n_x, n_y]\right) < 0 \\ 0 & \text{otherwise} \end{cases}$$

The next step in the processing is to group of object pixels in the binary image that are connected on their edges and assigned a unique label in step 62 to each region. All pixels in a connected region have the same intensity values, which for this case is 1, and are in some way connected with each other. The pixel connectivity can be defined in different ways, such as using the 4 or 8 nearest neighbors.

The result of the connected component analysis is to assign a region number to each pixel in the image $$L[n_x, n_y] = \{0, 1, 2, \ldots, N_{regions}\}$$

where $N_{regions}$ is the total number of regions and 0 represent is the null group corresponding to the noise pixels.

The final step 64 in this embodiment is to locate the objects within the connected components using some information about the anatomy of interest, such as the size and shape of the object or the direction of flow.

To use the size of the object, the area of each connected component can be calculated by counting the number of pixels in each region. The area for the $k^{th}$ connected component is $$A_k = A_{pixel} \sum_{nx,ny} L_k[n_x, x_y]$$

where $A_{pixel}$ is the area of the individual pixels and $L_k$ is a label indicating pixels in the $k^{th}$ connected component $$L_k[n_x, n_y] = \begin{cases} 1 & \text{if } L[n_x, n_y] = k \\ 0 & \text{otherwise} \end{cases}.$$

The regions containing the object can be found by comparing the component areas with a set of limits determined from the anatomy, $A_{min} \leq A_c \leq A_{max}$. The connected components that do not meet the size requirement are removed.

Once the region or regions containing an object has been identified, the center of the objects can be located using the maximum of the autocorrelation magnitude within the connected component or the centroid of the pixels for the connected component. An initial location of the edge of the object can also be found using a threshold to define a contour around the peak in the autocorrelation function or the outer edge of the connected component.

It is also possible to alternatively estimate the noise pixel statistics in step 58 (FIG. 6). Although, estimated statistics of the noise pixel may not exactly match the physiological scenario or the estimated noise parameter may not be optimal for a given application, an approximate measure of the statistics of the noise pixels may be sufficient to adapt a threshold for the automatic detection. Two example methods of estimating the noise statistics are described here, however the methods for estimating noise pixel statistics are not necessarily limited to these examples. Both of these example methods require less computation and may in some instances be less optimal than the methods that use actual noise pixel statistics.

The first embodiment of the steps for estimating noise pixel statistics uses the results of a separate hypothesis test for each truncated histogram to test the goodness of fit of the observed histogram to an ideal Rayleigh distribution. The values of the parameter for the Rayleigh distribution and the observed deviation for each truncated histogram are found using step 3 above. The hypothesis test makes a binary decision of whether to accept the null hypothesis, which, in this example, is that the histogram was generated from the Rayleigh distribution with the known parameter.

In the goodness of fit test, a $\chi^2$ distribution for the deviation is commonly assumed and a significance level is selected for the hypothesis test. The significance level is the probability that the null hypothesis will be rejected when it is true, this is referred to as a Type I error in statistics. A threshold for the deviation is found by inverting the $\chi^2$ cumulative distribution function to find the point that produces the specified significance level. The null hypothesis is accepted if the observed deviation is less than the calculated threshold.

Using the number of bins in the truncated histogram, the threshold on the deviation for a given confidence level can be calculated by $$\chi_{1-\alpha}^2(m) = F_\chi^{-1}(1-\alpha|m) = \{x : F_\chi(x|m) = 1-\alpha\}$$

where $F_{\chi^2}(x|m)$ is the CDF of the $\chi^2$ distribution with m degrees of freedom and $\alpha$ is the significance level. This is equivalent to the finding the point where the probability of correctly selecting the null hypothesis is $(1-\alpha)$ when the null hypothesis is true. A table of the thresholds for several degrees of freedoms can be pre-computed for a given significance level. A typical significant level used for this goodness of fit test is 5%.

The hypothesis test is a binary decision and the null hypothesis is accepted if $$q < \chi_{1-\alpha}^2(M-1).$$

To allow the multiple hypothesis tests from the different truncated histograms to be compared, a ratio is formed to indicate the amount by which the threshold is exceeded. The ratio is given by $$\lambda_n' = \frac{\chi_{1-\alpha}^2(M_n - 1)}{q_n}$$

and the null hypothesis is accepted if $\lambda_n' > 1$.

The index for the truncated histogram with the largest margin of exceeding the threshold can be selected as having the best fit, yielding $$n^* = \arg\max_n \{\lambda_n'\}$$

and the corresponding parameter for the Rayleigh distribution used to describe the noise statistics.

The second example embodiment of the steps for estimating noise pixel statistics eliminates the need for a search routine entirely by pre-selecting a percentage of the histogram to use as the truncated noise histogram. Then, the parameter for the Rayleigh distribution is calculated using an expression for the maximum likelihood estimate of this parameter assuming the samples were drawn from a true Rayleigh distribution. The maximum-likelihood estimate of the parameter in the Rayleigh distribution is $$\hat{s} = \sqrt{\frac{1}{2N_{pixels}} \sum_{i=0}^{N_{pixels}} z_i^2}$$

where $z_i$ is the amplitude of the $i^{th}$ pixels and $N_{pixel}$ is the total number of pixels in the frame.

As noted, another embodiment of the methods and systems uses the HR demodulation steps to enhance the appearance of objects with periodic motion on an ultrasound scanner display. The power, rather than the speed or the direction motion, of the Doppler signal after color flow processing and HR demodulation is reflected in the displayed image. The enhanced display is useful for a variety of application including, but not limited to, displaying small objects or objects will low velocities that are not easily visualized in a traditional display mode for Doppler imaging.

Figure 7:
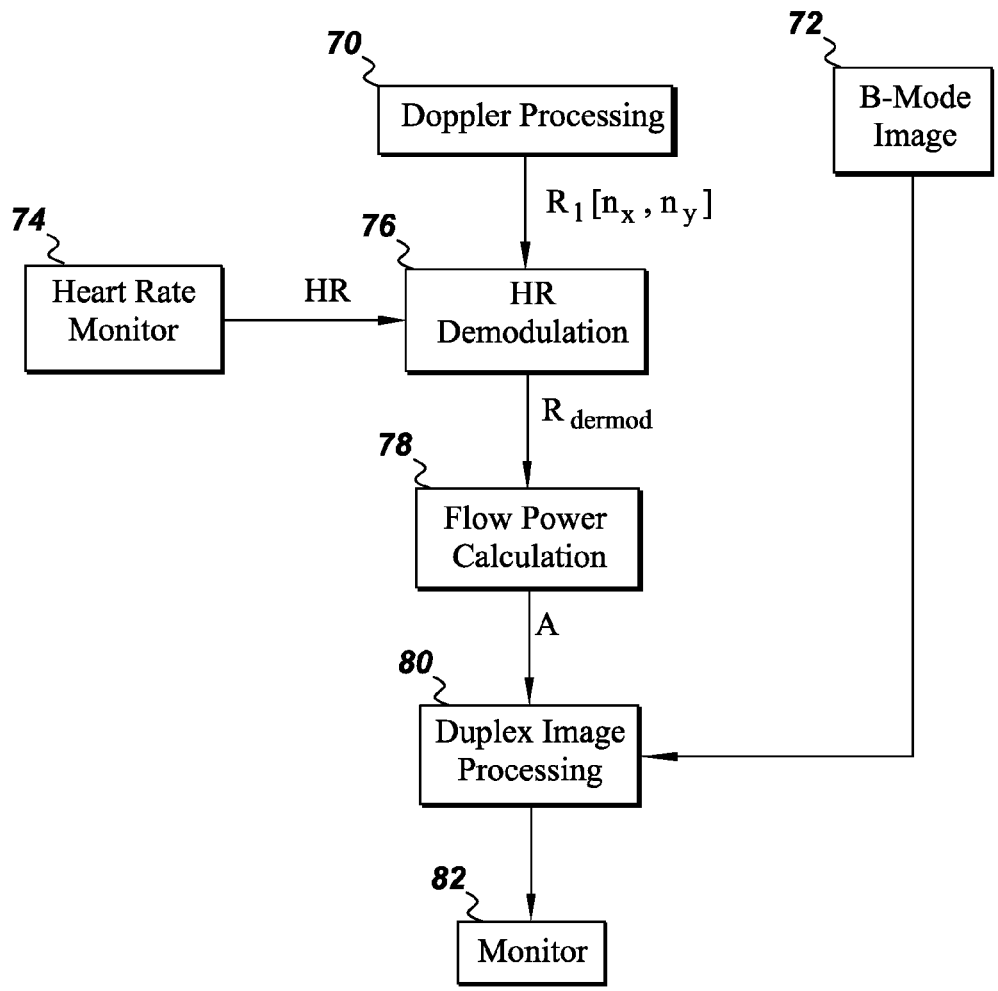
FIG. 7 is a block diagram of a plurality of steps in an embodiment of the methods and systems for object enhancement.

The steps of an embodiment of the methods and systems for enhancing a target object are generally shown in FIG. 7. The processing starts with the data 70 from a PW Doppler acquisition mode, blood flow or tissue velocity, with the ultrasound transducer held in approximately the same position and orientation for a number of cardiac cycles.

There are two interleaved data streams generated by the ultrasound system in PW Doppler mode, corresponding to the B-mode image data 72 and the Doppler data 70. The B-mode data undergoes the standard envelope detection and logarithmic compression used in ultrasound scanners to generate the B-mode images. The PW Doppler data is processed using standard Doppler processing techniques, either with or without the clutter filter, to form the complex autocorrelation pixels.

The heart rate demodulation step 76, using heart rate data from monitor 74, described previously, is applied to the complex autocorrelation function after Doppler processing. Next, the power of the HR demodulated signal is computed in step 78 by taking the magnitude of the complex autocorrelation pixels, $$A[n_x, n_y] = R_{demod}[n_x, n_y]^2$$

creating an image sequence with the pixels containing periodic motion enhanced.

The two image sequences, the B-Mode and the HR demodulated power Doppler, are then combined into a single image sequence for display by duplex display step 80. A duplex display mode simultaneously displays both the B-mode image using a grayscale colormap and the Doppler information using a color overlay. The duplex processing include the scan conversion that interpolates the pixel data from the two image sequences into a common reference frame with the correct geometrical aspect ratio. A grayscale map is used to encode the B-Mode image the power Doppler information is overlaid using a color map. The output of the processing is a sequence of color images, which are then sent to the display system and monitor 82.

The object enhancement processing can be run continuously as new frames are acquired. There is a start-up period due to the step response of the lowpass filter that is part of the HR demodulation. As such, it may take several cardiac cycles for the HR demodulation to reach a steady state and the display to represent the strength of the HR demodulated signal. If the probe is moved significantly over a short period of time, it may again take a number of cardiac cycles before the HR demodulation reaches a new steady state at the new probe position. It is sometimes beneficial to reset the algorithm when probe motion has been detected to avoid flashing of the color due to the large motion.

As noted, one or more embodiments of the rate demodulation based methods and system may be used to automatically detect an artery as part of an ultrasound-based monitoring device that measures hemodynamic parameters, such as blood pressure or the volumetric blood flow.

For example, one embodiment of an automatic objection detection system is a system used to detect a brachial artery with the ultrasound probe placed flat to the skin on the upper arm with the scan plan perpendicular to the long axis of the arm. This example comprises two data sets, one with the brachial artery in the field of view and the other without a larger artery included in the field of view.

Figure 8:
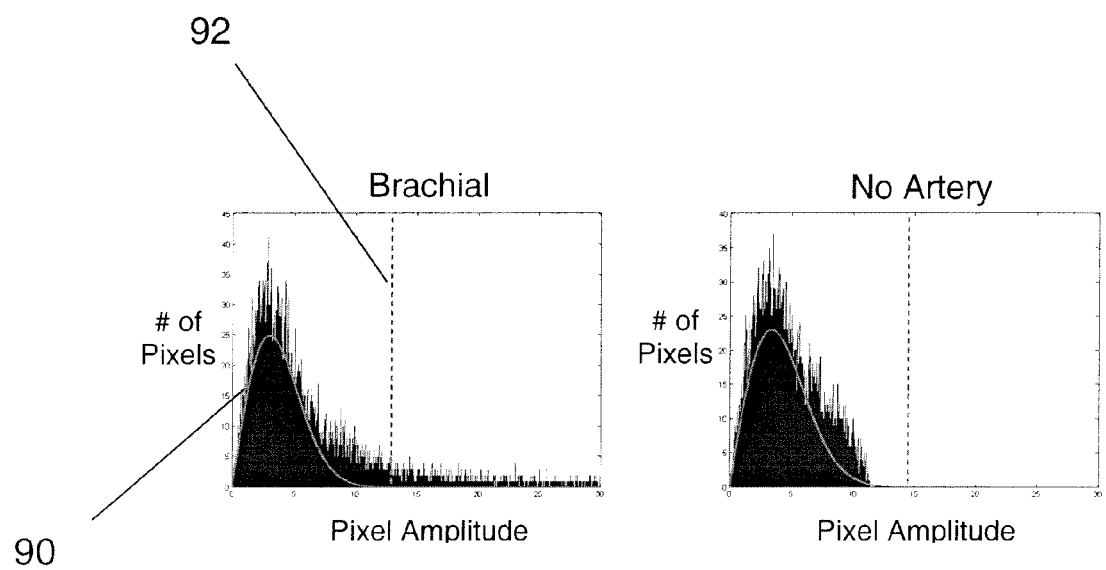
FIG. 8 shows two histograms of noise pixel amplitudes of embodiments of the methods and systems for automatic object detection showing the presence of a brachial artery and the absence of an artery.

The results of estimating the noise statistics for a truncated portion of the histogram for this embodiment are shown in FIG. 8 for the two examples. The curve 90 plotted along with the histogram is an expected occurrence for an ideal Rayleigh distribution using the parameter that best fitted the data. The dashed line 92 is the noise threshold calculated using $P_{FA} = 0.0001$. The values of threshold is quite similar between the two data sets, as would be expected since the noise properties should not change due of the inclusion of a artery in the field of view since the acquisition and processing parameters remain the same.

Figure 9:
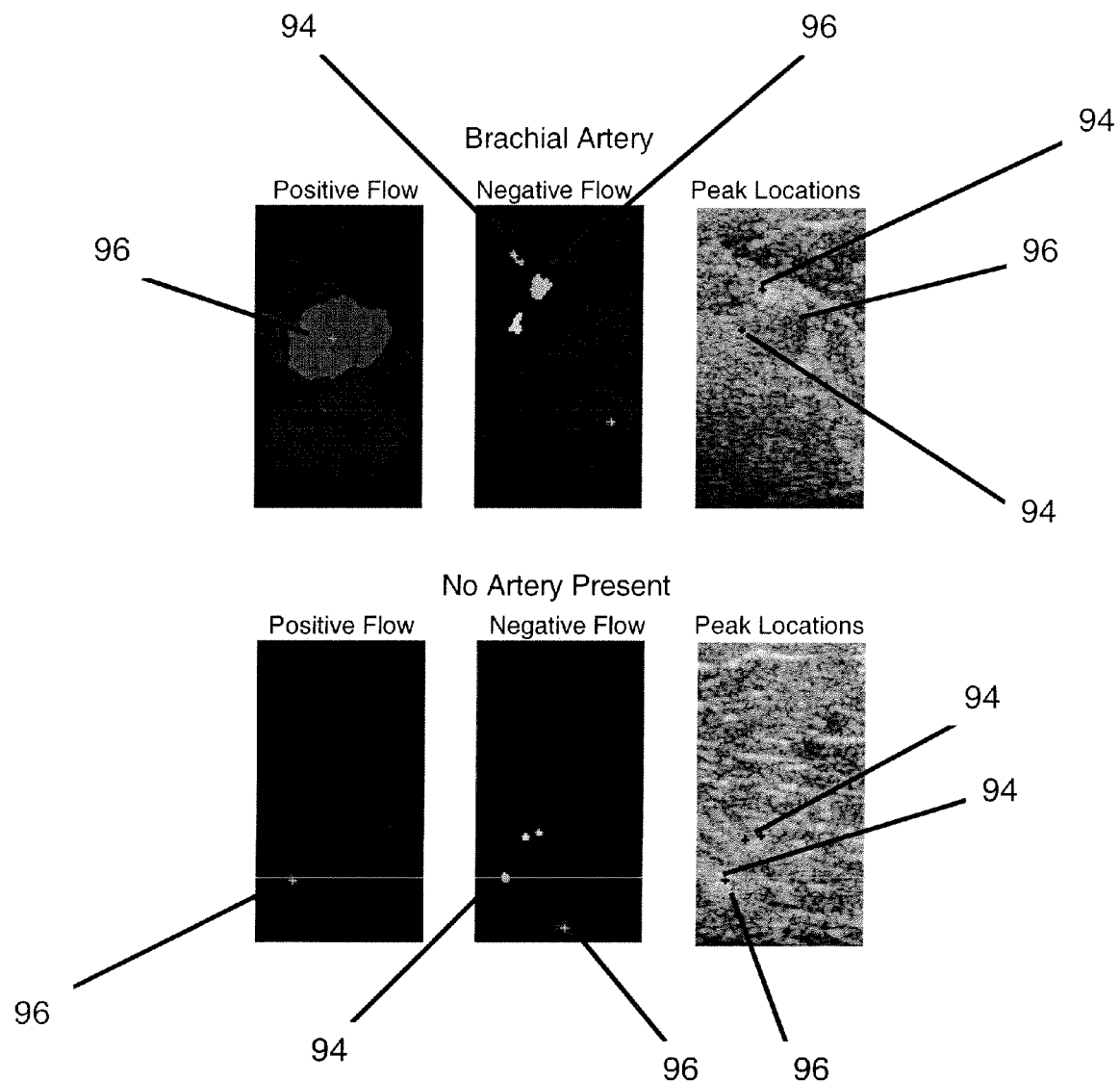
FIG. 9 shows a series of images reflecting embodiments of a connected component analysis showing the presence of a brachial artery and the absence of an artery.

Using the threshold calculated from the noise statistic, the connected component analysis for the positive flow and negative flow pixels are shown in FIG. 9 in which the noise pixels. The locations of the peaks within each connected component are indicated with markers in the B-mode image for the same region of interest, 96 for positive flow and 94 for negative flow.

Figure 10:
FIG. 10 shows two images from an embodiment of the methods and systems for automatic object detection using size constraint on connected components showing the presence of a brachial artery and the absence of an artery.
Figure 10:
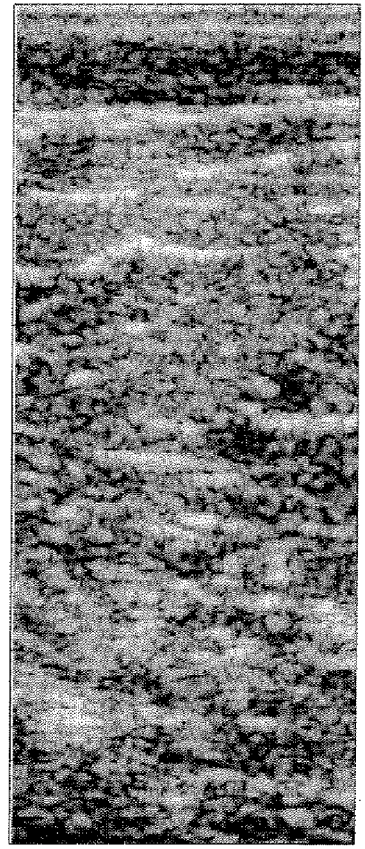

The results shown in FIG. 10 reflect applying a size constraint to the connected components. An initial estimate of the edge of the artery may be found by averaging the 6 dB peak widths in the x and y directions for the autocorrelation magnitudes.

Figure 11:
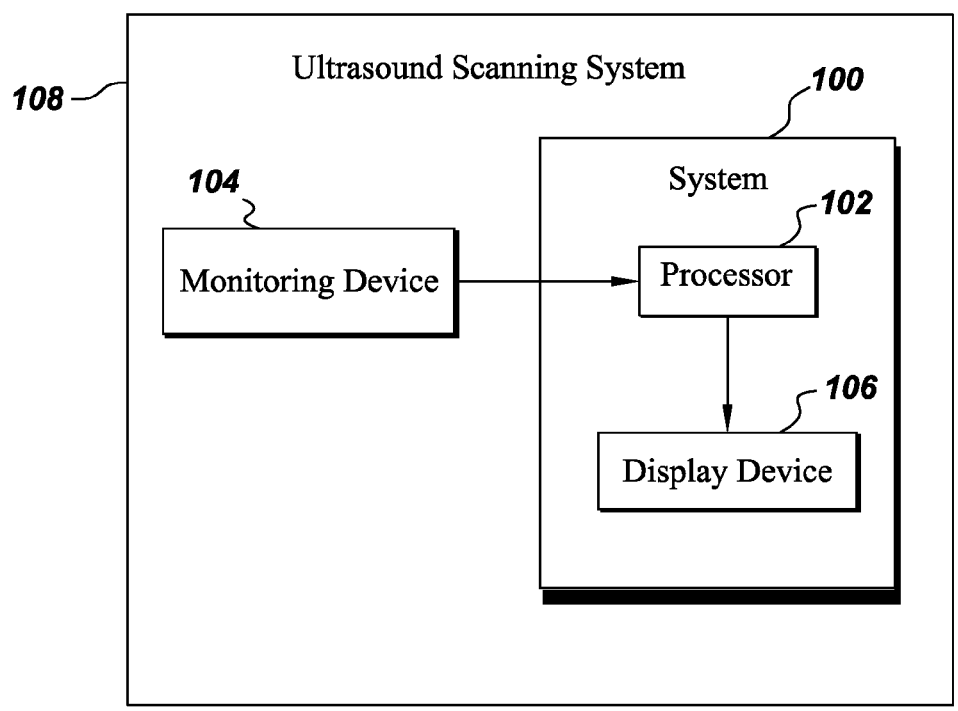
FIG. 11 is a block diagram of an embodiment of the system for carrying out one or more of the methods.

The methods may be embodied in an imaging system, such as an ultrasounds scanning system. One embodiment of the system is shown in FIG. 11 and is generally referred to as imaging system 100. System 100 is an embodiment of a system for automatically detecting an object associated with a rate of movement. System 100 may also be configured to enhance or amplify the signal of any target object associated with a movement, such as, but not limited to, an arterial vessel or vein, or a fetal heart.

The rate of movement in this example embodiment is an individual's heart rate that is derived from a heart-monitoring device 102. Heart monitoring device may be any number of sources currently available or that may become available that is capable of measuring an individual's heart rate directly or indirectly. If system 100 is using real time heart rate measurements than heart-monitoring device 102 needs to communicate directly with processor 104 or else data reflecting the heart rate of the individual will need to be entered through a data entry device into processor 104. Processor 104 may be configured as a component of an ultrasound scanning system 108 or as a stand-alone system.

System 100 generally comprises: a processor 104 for filtering a complex autocorrelation signal corresponding to the rate of movement; demodulating the filtered complex autocorrelation signal; calculating one or more statistics of one or more pixels corresponding to one or more non-moving noises; determining an adaptive threshold for a magnitude of one or more object pixels based on one or more properties of the noise; identifying the object pixels that correspond to one or more positive and negative velocities based on the threshold; assigning labels to one or more of the object pixels that are substantially adjacent; locating the adjacent object pixels that define one or more of the objects based on one or more size and power criteria; and creating an image that comprises one or more of the detected objects; and a display device 106 for displaying the image of the detected object. The system may also comprise a printer for printing out images, data and/or reports and may also be configured to transmit the images, data or reports to remote locations. The reports may comprise the images, data and/or analytical conclusions about the images. The information may be transmitted, using a hard wire connection or wirelessly, over a local area network, the Internet or satellite, or any other suitable means of transmission.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for enhancing a signal of a target object comprising the steps of,
providing a rate of movement of said target object;
demodulating a signal with said rate of said target object;
calculating one or more statistics of one or more pixels corresponding to one or more non-moving noises;
determining an adaptive threshold for a magnitude of one or more object pixels based on one or more properties of said noise;
identifying said object pixels that correspond to one or more positive and negative velocities based on said threshold;
assigning labels to one or more of said object pixels that are substantially adjacent; and
locating said adjacent object pixels that define one or more objects based on one or more size and power criteria.

2. A system for automatically detecting an object associated with a rate of movement, comprising,
a processor for:
filtering a complex autocorrelation signal corresponding to said rate of movement;
demodulating said filtered complex autocorrelation signal;
calculating one or more statistics of one or more pixels corresponding to one or more non-moving noises;
determining an adaptive threshold for a magnitude of one or more object pixels based on one or more properties of said noise;
identifying said object pixels that correspond to one or more positive and negative velocities based on said threshold;
assigning labels to one or more of said object pixels that are substantially adjacent;
locating said adjacent object pixels that define one or more of said objects based on one or more size and power criteria; and
creating an image that comprises a location of one or more of said detected objects; and
a display device for displaying said image of said detected object.

* * * * *